United States Patent [19]
Brown et al.

[11] Patent Number: 5,129,511
[45] Date of Patent: Jul. 14, 1992

[54] PACKAGE FOR A COMBINED SURGICAL SUTURE-NEEDLE DEVICE

[75] Inventors: David L. Brown, Wallingford; Henry A. Holzwarth, Weston, both of Conn.

[73] Assignee: United States Surgical Corporation, Norwalk, Conn.

[21] Appl. No.: 601,019

[22] Filed: Oct. 18, 1990

Related U.S. Application Data

[63] Continuation of Ser. No. 388,152, Aug. 1, 1989, abandoned.

[51] Int. Cl.$^5$ .............................. A61B 17/06
[52] U.S. Cl. ........................ 206/63.3; 206/339
[58] Field of Search ................ 206/63.3, 438, 382, 206/339

[56] References Cited

U.S. PATENT DOCUMENTS

| | | | |
|---|---|---|---|
| 121,860 | 12/1871 | Evans | 206/382 |
| 1,357,128 | 10/1920 | Travis | 206/63.3 |
| 2,615,565 | 10/1952 | Bower et al. | 206/63.3 |
| 2,917,878 | 12/1959 | Carnarius et al. | 53/22 |
| 2,949,181 | 8/1960 | Buccino | 206/63.3 |
| 2,965,225 | 12/1960 | Zoller et al. | 206/63.3 |
| 3,043,067 | 7/1962 | Rynkiewicz et al. | 53/27 |
| 3,143,209 | 8/1964 | Turiansky | 206/63.3 |
| 3,147,861 | 8/1964 | Kurtz | 206/63.3 |
| 3,163,288 | 12/1964 | Arvidsson | 206/63.3 |
| 3,189,174 | 6/1965 | Cormack | 206/63.3 |
| 3,202,273 | 8/1965 | Riall | 206/63.3 |
| 3,221,873 | 12/1965 | Bowes et al. | 206/63.3 |
| 3,256,981 | 6/1966 | Kurtz | 206/56 |
| 3,280,971 | 10/1966 | Relan, Jr. | 206/63.3 |
| 3,301,393 | 1/1967 | Regan, Jr. et al. | 206/63.3 |
| 3,315,802 | 4/1967 | Lonholdt et al. | 206/56 |
| 3,319,782 | 5/1967 | Bowes | 206/63.3 |
| 3,338,019 | 8/1967 | Trewella et al. | 206/63.3 |
| 3,338,401 | 12/1967 | Regan, Jr. | 206/63.3 |
| 3,357,549 | 12/1967 | Staiti | 206/63.3 |
| 3,495,703 | 2/1970 | Calabrese | 206/63.3 |
| 3,613,879 | 10/1971 | Kemble | 206/63.3 |
| 3,627,120 | 12/1971 | Bordeau | 206/63.3 |
| 3,642,126 | 2/1972 | Kurtz et al. | 206/63.3 |
| 3,648,949 | 3/1972 | Berger et al. | 206/63.3 |
| 3,731,793 | 5/1973 | Hagel | 206/63.3 |
| 3,876,068 | 4/1975 | Sonnino | 206/63.3 |
| 3,939,969 | 2/1976 | Miller et al. | 206/63.3 |
| 3,972,418 | 8/1977 | Schuler et al. | 206/63.3 |
| 4,014,433 | 3/1977 | Cerwin | 206/63.3 |
| 4,069,912 | 1/1978 | Black et al. | 206/63.3 |
| 4,084,692 | 4/1978 | Bilweis | 206/63.3 |
| 4,089,410 | 5/1978 | Bolanowski | 206/63.3 |
| 4,131,195 | 12/1978 | Worrell, Sr. | 206/205 |
| 4,135,623 | 1/1979 | Thyen | 206/63.3 |
| 4,168,000 | 9/1979 | MacRitchie | 206/63.3 |
| 4,192,420 | 3/1980 | Worrell, Sr. et al. | 206/205 |
| 4,249,656 | 2/1981 | Cerwin et al. | 206/63.3 |
| 4,261,463 | 4/1981 | Shave | 206/63.3 |
| 4,284,194 | 8/1981 | Flatau | 206/63.3 |
| 4,369,880 | 1/1983 | Giggey et al. | 206/63.3 |
| 4,533,041 | 8/1985 | Aday et al. | 206/63.3 |
| 4,549,649 | 10/1985 | Roshoy | 206/63.3 |

Primary Examiner—Paul T. Sewell
Assistant Examiner—Jacob K. Ackun, Jr.
Attorney, Agent, or Firm—Thomas R. Bremer; Peter G. Dilworth; Rocco S. Barrese

[57] ABSTRACT

A package is provided for a combined surgical suture-needle device featuring a peelable, or strippable, closure flap.

8 Claims, 3 Drawing Sheets

PACKAGE FOR A COMBINED SURGICAL SUTURE-NEEDLE DEVICE

This is a continuation of copending application Ser. No. 07/388,152 filed on Aug. 1, 1989, now abandoned.

BACKGROUND OF THE INVENTION

This invention relates to a package for a combined surgical suture-needle device. More particularly, this invention relates to a moisture-impervious sterile package featuring a peelable closure flap terminating in a tab which facilitates gripping of the flap in the course of its being opened.

Many types of packages for sutures and combined surgical suture-needle devices are known in the art including those described in U.S. Pat. Nos. 2,917,878; 2,949,181; 2,965,225; 3,043,067; 3,143,209; 3,147,861; 3,163,288; 3,202,273; 3,221,873; 3,256,981; 3,280,971; 3,315,802; 3,319,782; 3,338,401; 3,357,549; 3,613,879; 3,627,120; 3,642,126; 3,648,949; 3,876,068; 3,939,969; 4,014,433; 4,069,912; 4,089,410; 4,135,623; 4,168,000; 4,249,656; 4,261,463; 4,284,194; 4,369,880; and, 4,549,649. Moisture-impervious packages possessing peelable, or strippable, closure flaps intended for the packaging of premoistened sheets are disclosed in U.S. Pat. Nos. 4,131,195 and 4,192,420.

Most surgical suture-needle packages in current use consist of a folded paper surgical suture-needle retainer seated within a sterile outer envelope. The sterility of the surgical suture-needle and envelope are maintained by a second sealed overwrap. When the surgical suture-needle is to be used, the overwrap is opened in the operating room and the sealed envelope is placed within the sterile field. Sterile personnel then tear open the sterile envelope to gain access to the surgical suture-needle.

Efforts have been made to improve this type of package to facilitate removal of the surgical suture-needle therefrom. In one known type package, a portion of the inner suture retainer is secured to the sealed envelope so that the envelope and the inner retainer can be opened simultaneously and the end of the suture exposed for immediate pickup. A drawback to this arrangement is that after the envelope is torn open, the torn portion many times separates from the envelope and is loose in the operating room. In addition, the needle component is often difficult to locate.

In another known type of package, a peelable envelope features two laminates which are bonded to each other. An access area at the top of the envelope is provided to enable the user to open the envelope by peeling the laminates apart. A difficulty with this design is that the user must regrasp the envelope prior to removal of the suture, a time consuming and undesirable activity. Furthermore, there is no stop point when peeling open the envelope so that the envelope is frequently opened too far with the inner retainer falling out.

SUMMARY OF THE INVENTION

It is a principal object of the present invention to provide a package for a combined surgical suture-needle device which, in the sealed condition, reliably maintains its contents in a sterile condition for an indefinite period, is substantially moisture-impervious, accommodates a wide variety of sutures and surgical needle combinations, and is readily opened for convenient access of its contents which are consistently oriented in a way facilitating their removal from the package.

It is a particular object of the invention to provide such a package possessing a pocket-like, suture-needle retainer featuring an integral, peelable, i.e., strippable, closure flap terminating in a tab which facilitates the gripping of the flap in the course of its being peeled away to provide ready access to the contents of the package.

In keeping with these and other objects of the invention, there is provided a package for a combined surgical suture-needle device which comprises:

a) an outer envelope of substantially moisture-impervious material characterized by longitudinal side edges and top and bottom transverse edges, the envelope including first and second walls adhered to each other along their edges to define an accessible pocket between them for receiving a combined surgical suture-needle device retainer member;

b) a closure flap hingedly adhered to a peripheral portion of one of said first and second walls and sealing access to the pocket of the outer envelope, the closure flap terminating in a grip-facilitating tab whose free edge terminates a distance away from the bottom transverse edge of the outer envelope; and, c) a combined surgical suture-needle device retainer member received within the pocket of the outer envelope.

The foregoing surgical suture-needle package possesses several advantages over known packages such as those described in the cited prior art. Thus, the peelable closure flap feature involves only one step to open the package, allowing access to the suture-needle combination contained therein without the need to regrasp the package, and results in less effort being expended to accomplish this than the tear feature of known types of surgical suture-needle packages. In one embodiment of a suture-needle device retainer member which will be described herein in detail, a fold-over panel associated with the retainer and adhesively bonded to a portion of the interior surface of the peelable closure flap assures that following the opening of the package, the closure flap will remain secured to the remainder of the package. Such an arrangement represents a simple and effective solution to the over-tearing problem which can occur on opening the known types of surgical suture-needle packages referred to earlier.

BRIEF DESCRIPTION OF THE DRAWINGS

In the accompanying drawings in which like numerals are used to refer to like elements throughout.

DESCRIPTION OF THE PREFERRED EMBODIMENTS

Figure 1:
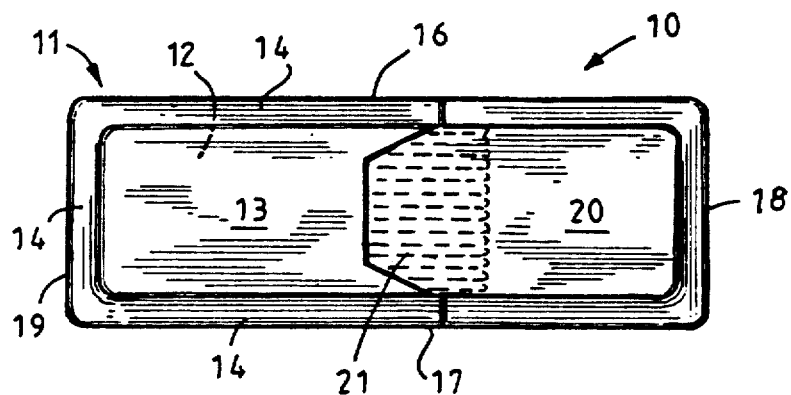
FIG. 1 is a top plan view of a package in accordance with this invention showing the closure flap in the closed condition.
Figure 2:
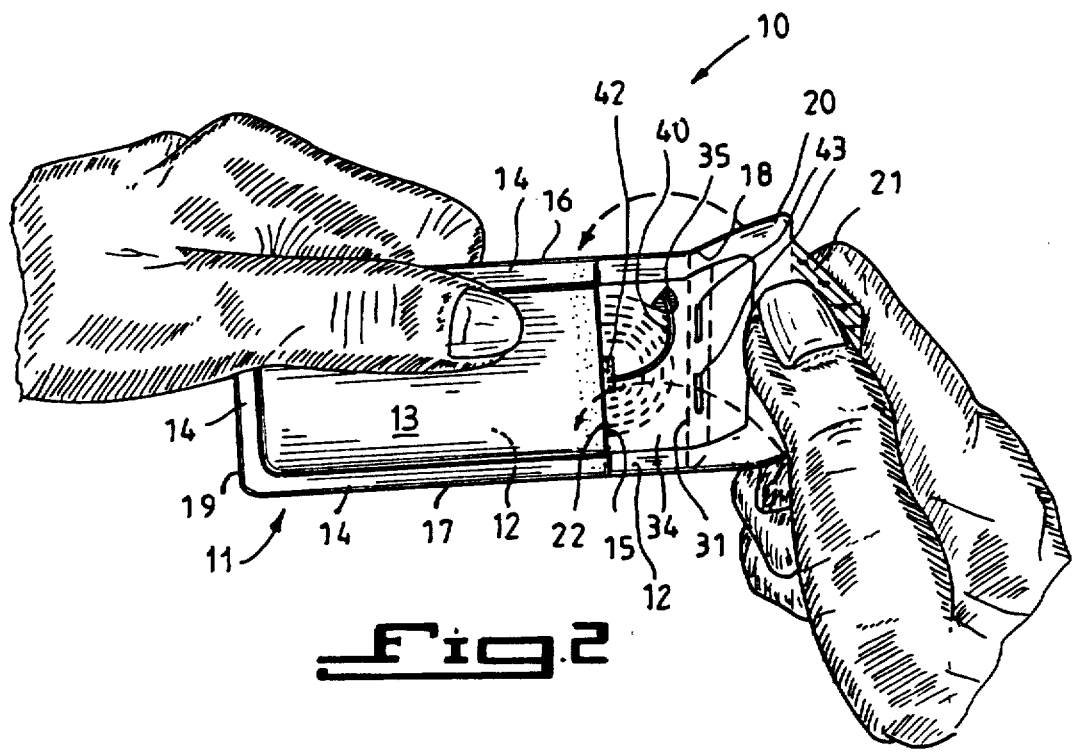
FIG. 2 illustrates the package of FIG. 1 with the closure flap being peeled away to provide access to the package contents.

Referring to FIGS. 1 and 2, suture package 10 comprises an outer envelope 11 made up of a first wall 12 and a second wall 13 adhered to each other along their common edges 14 employing any known and conventional adhesive.

Outer envelope 11 is characterized by longitudinal side edges 16 and 17 and top and bottom transverse edges 18 and 19.

The material of construction of walls 12 and 13 and peelable closure flap 20 is one which prevents or greatly impedes the transmission of moisture therethrough. In the embodiment shown, walls 12 and 13 and closure flap 20 are of laminate construction of a known type in which an aluminum foil is faced on its interior side with a polyolefin film such as polyethylene film. The laminate can vary in thickness from about 3 to about 5 mils and preferably from about 3.5 to about 4.5 mils.

The top transverse edge 22 of second wall 13 terminates a sufficient distance from perforate score line 31 of fold-over panel 32 of surgical suture-needle device retainer member 30 as to expose a portion of surgical needle 40 and foamed needle holder 42. In the sealed condition of the package as shown in FIG. 1, peelable closure flap 20 completely seals pocket 15 of outer envelope 11 thus maintaining the contents of the package in the sterile condition. To facilitate the opening of sealed package 10, closure flap 20 is provided with a generally trapezoidal-shaped, knurled tab 21 which terminates some distance away from bottom transverse edge 19 of sealed envelope 11. Advantageously, the free edge of tab 21 terminates at a point which lies from about 20 to about 80%, and preferably from about 40 to about 60%, of the length of outer envelope 11 as measured from its top transverse edge 18. In the embodiment shown, this edge lies at a point which is about 50% of this length, i.e., at about the mid-point of the package. In addition to making it easier to grip closure flap 20, the knurling of tab 21 carries with it the advantage that any material shrinkage or deformation caused by the heat sealing of the flap will tend to go unnoticed.

To open sealed package 10, tab 21 is gripped in one hand, outer suture envelope 11 is gripped with the other and with a peeling or stripping motion, closure flap 20 is separated from its zone of adherent contact with wall 13 to expose needle 40. After package 10 has been opened, closure flap 20 remains hingedly attached to the top transverse edge 18 of outer envelope 11. To prevent an excessively forceful peeling motion from resulting in the complete detachment of closure panel 20 from transverse edge 18 of outer envelope 11, the reverse side of fold-over panel 32 is adhesively secured to a portion of the interior face of closure panel 20. In addition to providing this function, fold-over panel 32 in the closed condition of the package provides additional security against an accidental puncturing of the outer envelope by needle 40. Rectangular cutouts 43 in fold-over panel 32 facilitate the circulation of gaseous sterilizing agent, e.g., ethylene oxide, in and around needle 40 during the sterilization of the package contents.

Figure 3:
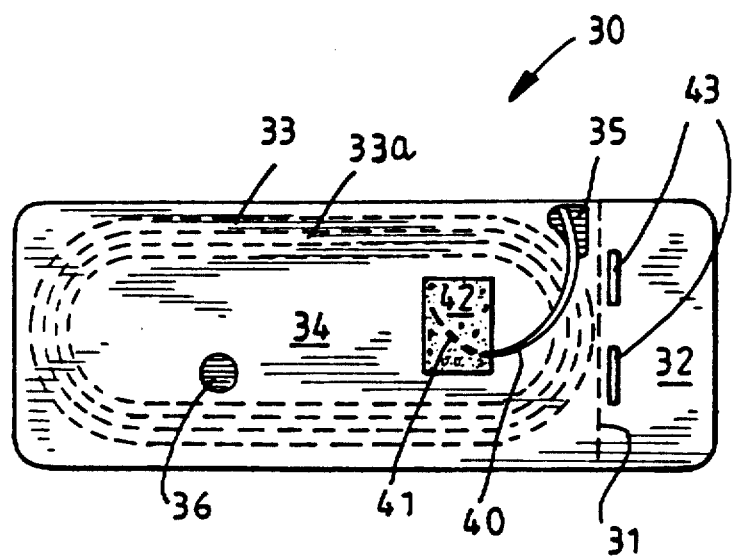
FIGS. 3 and 4 are obverse and reverse plan views, respectively, of the combined suture-needle device retainer member of the package of FIG. 1; and, FIGS. 5 and 6 are plan views of another embodiment of suture-needle retainer shown in the fully unfolded and fully folded conditions, respectively.

Referring to FIG. 3, surgical suture-needle device retainer member 30 includes a generally flat foil or sheet 33 having a main panel 34 and fold-over panel 32 joined to the main panel along perforate score line 31. The sharp tip 41 (indicated by the dotted line) of needle 40 is held within foamed needle holder 42 preventing or minimizing accidental puncture of outer envelope 11 (FIG. 1). An approximately triangular shaped aperture 35 is provided at one corner of main panel 34 through which the blunt tip of the needle and/or its attached suture passes. A circular aperture 36 is provided on main panel 34 in order to allow the suture to be vacuum-loaded into coiled passageway 38. To remove the combined surgical suture-needle device, grasping the exposed section of needle 40 by forceps, the tip of the needle is removed from foamed needle holder 42 and the needle with its attached length of suture is withdrawn from retainer member 30.

Figure 4:
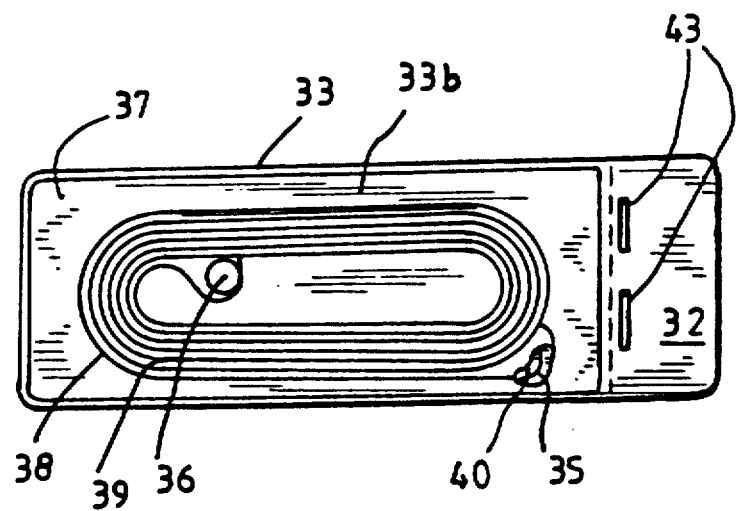

As shown in FIG. 4, a molded suture-retaining reel or labyrinth 37 possessing a coiled passageway 38 for suture 39 is mounted upon the reverse side of main panel 34. When fully positioned within pocket 15 of outer envelope 11 (FIG. 1), face 33b of suture-retaining reel 37 is in non-adherent contact with the inner surface of first wall 12 and the external surface 33a of main panel 33 is in non-adherent contact with the inner surface of second wall 13.

Figure 5:
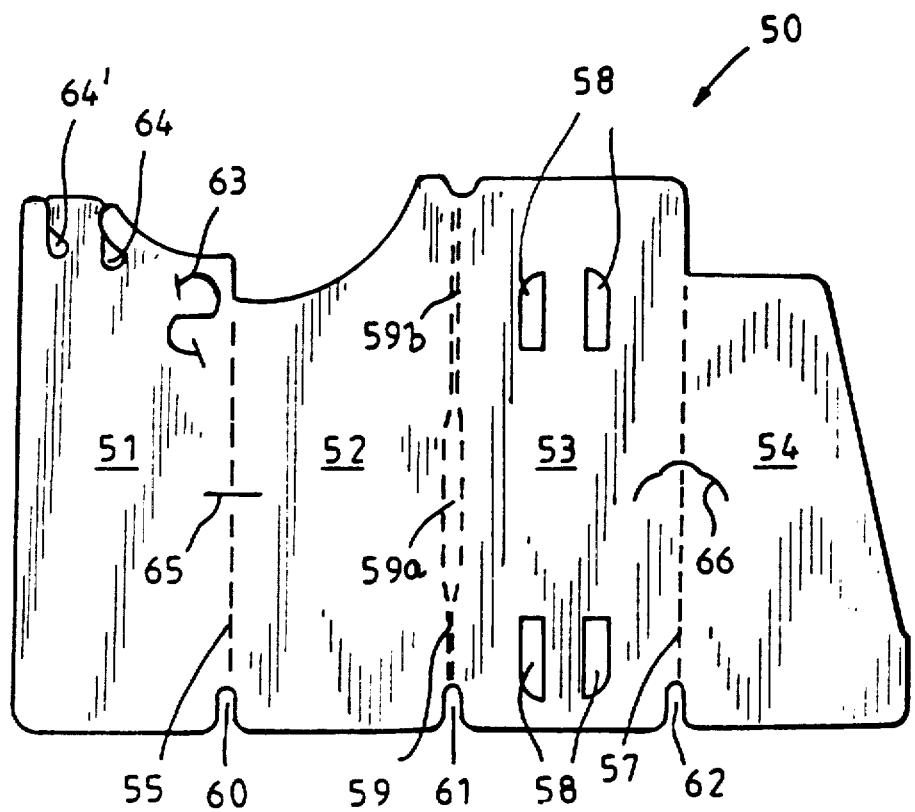
Figure 6:
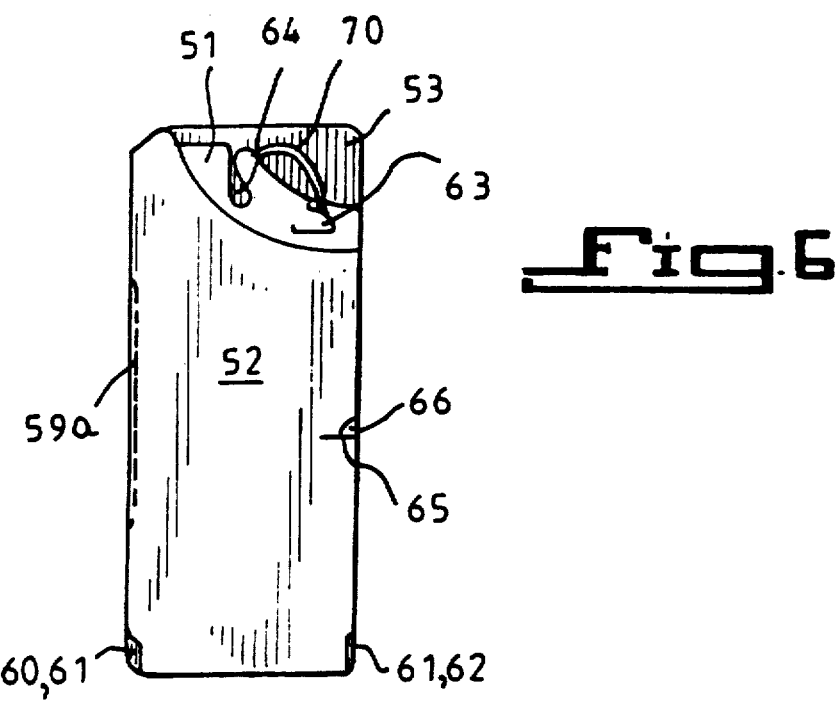

FIG. 5 illustrates a fully unfolded surgical sutre-needle device retainer member 50 which can also be used in the package of this invention and FIG. 6 illustrates retainer 50 in the fully folded condition which it assumes when received within the pocket of the package.

Retainer member 50 is made up of four panels, namely, needle retaining panel 51, front cover panel 52', suture winding panel 53 (which also functions as the rear panel of the fully folded retainer) and fold-over panel 54. Retainer member 50 is preferably formed from a single sheet of suitable material, e.g., stiff paper or paperboard such as 5 point to 12 point solid, bleached sulfate board, plastics, foils, laminates, and the like, which is die cut to provide the desired configuration. The panels are joined to each other along perforate, or score, lines 55, 59 and 57 which facilitate their folding and central gusset sections 59a and 59b provide a space or clearance between panels 52' and 53. Die cut 65 cooperates with die cut 66 to provide a snap-lock feature which maintains the retainer in the fully folded condition. Rounded indentations 60, 61 and 62 serve to prevent the suture from becoming caught between the panels when folded.

To load needle 70 with its attached suture 71 into retainer 50, the retainer is first secured in place by means of loading pins (not shown) which project through openings 58 in panel 53. The point of needle 70 is then inserted in die cut 63 which is shaped somewhat like a reversed "S" by threading the point under the upper, and then over the lower, half of the reversed "S" cut and then behind panel 51 so that the needle shank and tip are on opposite sides of panel 51. Slight tension is maintained on suture 71 from this stage of the loading procedure to the conclusion of the procedure to ensure that needle 70 will maintain its placement in die cut 63 as previously described. The shank of needle 70 is then threaded through one of teardrop-shaped cutouts 64 or 64', cutout 64 being used for smaller needles (as shown in FIG. 6) and cutout 64' being used for larger needles. After panel 51 has been folded over onto panel 52, suture 71 is wound in a figure "8" pattern around the loading pins projecting through openings 58 in panel 53. Retainer 50, now loaded with needle 70 and attached suture 71, is released from the loading pins, panel 54 is folded over on panel 53 and the partly folded-over structure is given a final folding along perforate line 61 and gussets 59a and 59b. Finally, a slight counter-directional movement of the upper section of the retainer against its lower section sets the aforementioned snap-lock in place providing the fully assembled, loaded retainer of FIG. 6.

What is claimed is:

1. A package for a combined surgical suture-needle device which comprises:
   a) an outer envelope of substantially moisture impervious material characterized by longitudinal side edges and top and bottom transverse edges, the envelope including first and second walls adhered to each other along their edges to define an accessible pocket between them for receiving a combined surgical suture-needle device retainer member;
   a peelable closure flap hingedly adhered to an outer peripheral portion of said first wall and sealing access to the pocket of the outer envelope, the closure flap terminating in a grip-facilitating tab whose free edge terminates a distance away from the bottom transverse edge of the outer envelope; and
   c) a combined surgical suture-needle device retainer member received within the pocket of the outer envelope;
   wherein the top transverse edge of said second wall terminates a sufficient distance from the top transverse edge of said first wall to which said closure flap hingedly adheres, to expose a portion of a surgical needle retained in said retainer member when said flap is peeled;
   said combined surgical suture-needle device retainer member (c) includes a panel being subdivided into a main panel portion and a fold-over panel portion attached to the main panel portion along a score line; and
   the bottom surface of the fold-over panel portion being adherently secured to a portion of the interior surface of the closure flap;
   whereby said package is opened in a single step by peeling of said closure flap, allowing access to the suture-needle combination contained therein without need to regrasp said package.

2. The package of claim 1 wherein said outer envelope (a) and closure flap (b) are fabricated from a laminate.

3. The package of claim 1 wherein said outer envelope (a) and closure flap (b) are fabricated from a laminate including an exterior surface layer of aluminum and an interior surface layer of a polyolefin.

4. The package of claim 1 wherein the free edge of the grip-facilitating tap of said closure flap (b) terminates at a point which lies at a distance of from about 20 to 80% of the length of the outer envelope as measured from the top transverse edge thereof.

5. The package of claim 1 wherein the free edge of the grip-facilitating tab of said closure flap (b) terminates at a point which lies at a distance of from about 40 to about 60% of the length of the outer envelope as measured from the top transverse edge thereof.

6. The package of claim 1, wherein said main panel has a mounting surface upon which a suture-retaining labyrinth is mounted and an aperture is provided through which a suture enclosed within said labyrinth passes upon removal of the combined surgical suture-needle device.

7. The package of claim 1, wherein said score line is a perforate score line.

8. The package of claim 1, wherein said peelable closure flap (b) is provided with a generally trapezoidal-shaped, knurled tab terminating at a point away from said bottom transverse edge of said outer envelope.

9. The package of claim 1, wherein said closure flap (b) is arranged to open in the longitudinal direction of said envelope (a).

10. The package of claim 1, wherein said retainer member (c) adheres to said closure flap (b) when said closure flap (b) is peeled away from said second wall.

11. A package for a combined surgical suture-needle device which comprises:
   a) an outer envelope of substantially moisture impervious material characterized by longitudinal side edges and top and bottom transverse edges, the envelope including first and second walls adhered to each other along their edges to define an accessible pocket between them for receiving a combined surgical suture-needle retainer member;
   b) a peelable closure flap hingedly adhered to a peripheral portion of said first wall and sealing access to the pocket of the outer envelope, the closure flap terminating in a grip-facilitating tab whose free edge terminates a distance away from the bottom transverse edge of the outer envelope; and
   c) a combined surgical suture-needle retainer member received within the pocket of the outer envelope;
   wherein the top transverse edge of said second wall terminates a sufficient distance from the bottom transverse edge of said first wall to which said closure flap hingedly adheres, to expose a portion of a surgical needle retained in said retainer member when said flap is peeled;
   wherein said combined surgical suture-needle device retainer member (c) includes a flat panel having an exposed bottom surface and a suture-retaining labyrinth mounting surface;
   the panel being sub-divided into a main panel portion and a fold-over panel portion attached to the main panel portion along a perforate score line;
   a suture retaining labyrinth mounted upon the suture-retaining labyrinth mounting surface of the flat panel and an aperture in the main panel portion through which a suture enclosed within the labyrinth passes upon removal of the combined surgical suture-needle device;
   the bottom surface of the fold-over panel portion being adherently secured to a portion of the interior surface of the closure flap;
   the bottom surface of the main panel portion being in non-adherent contact with the interior surface of the first wall of the outer envelope and the exposed surface of the suture-retaining labyrinth being in non-adherent contact with an interior surface of the second wall of the outer envelope;
   whereby said package is opened in a single step by peeling of said closure flap, allowing access to the suture-needle combination contained herein without need to regrasp said package.

12. The package of claim 11 wherein the fold-over panel portion possesses at least one passage for facilitating the circulation of gas therethrough.

13. The package of claim 11, wherein said aperture in said panel portion is situated adjacent to said fold-over portion, and said closure flap (b) is arranged to open in the longitudinal direction of said envelope (a).

14. A package for a combined surgical suture-needle device which comprises:
   a) an outer envelope of substantially moisture impervious material characterized by longitudinal side edges and top and bottom transverse edges, the envelope including first and second walls adhered to each other along their edges to define an accessible pocket between them for receiving a combined surgical suture-needle device retainer member;

b) a peelable closure flap hingedly adhered to a peripheral portion of said first wall and sealing access to the pocket of the outer envelope, he closure flap terminating in a grip-facilitating tab whose free edge terminates a distance away from the bottom transverse edge of the outer envelope; and c) a combined surgical suture-needle device retainer member received within the pocket of the outer envelope;

wherein said combined surgical suture-needle device retainer member (c) includes means for exposing at least a portion of at least one of a needle and an attached suture upon peeling of said closure flap (b) and a main panel having a mounting surface upon which a suture-retaining labyrinth is mounted, an aperture being provided through which a suture enclosed within said labyrinth passes upon removal of the combined surgical suture-needle device; and a fold-over panel attached to the mounting surface of said main panel along a score line, the bottom surface of said fold over panel adherently secured to a portion of the interior surface of said closure flap;

whereby said package is opened in a single step by peeling of said closure flap, allowing access to the suture-needle combination contained therein without need to regrasp said package.

15. The package of claim 14, wherein said retainer member (c) adheres to said closure flap (b) when said closure flap (b) is peeled away from said second wall.

16. The package of claim 14, wherein said closure flap (b) is arranged to open in the longitudinal direction of said envelope (a).

17. A package for a combined surgical suture-needle device which comprises:

a) an outer envelope of substantially moisture impervious material characterized by longitudinal side edges and top and bottom transverse edges, the envelope including first and second walls adhered to each other along their edges to define an accessible pocket between them for receiving a combined surgical suture-needle device retainer;

b) a peelable closure flap hingedly adhered to a peripheral portion of said first wall and sealing access to the pocket of the outer envelope, the closure flap terminating in a grip-facilitating tab whose free edge terminates a distance away from the bottom transverse edge of the outer envelope; and c) a combined surgical suture-needle device retainer member received within the pocket of the outer envelope;

wherein the top transverse edge of said second wall terminates a sufficient distance from the top transverse edge of said first wall to which said closure flap hingedly adheres, to expose a portion of a surgical needle retained in said retainer member when flap is peeled opened;

wherein said retainer member (c) possesses means for adhering to said closure flap (b) when said closure flap (b) is peeled away from said second wall;

wherein said retainer member (c) includes a main panel portion for retaining the suture and fold-over panel portion attached to the main panel portion along a score line;

said means for adhering said retainer member (c) to said closure flap (b) comprising the bottom surface of said fold-over panel portion being adherently secured to the interior surface of said closure flap (b); and said main panel portion in non-adherent contact with said outer envelope (a);

whereby said package is opened in a single step by opening of said closure flap, allowing access to the suture-needle combination contained therein without need to regrasp said package and whereby complete detachment of said closure flap (b) from said outer envelope (a) when said flap is peeled, and accidental puncturing of said outer envelope (a) by the needle when said flap (b) is closed, are both prevented.

18. A package for a combined surgical suture-needle device which comprises:

a) an outer envelope of substantially moisture impervious material characterized by longitudinal side edges and top and bottom transverse edges, the envelope including first and second walls adhered to each other along their edges to define an accessible pocket between them for receiving a combined surgical suture-needle device retainer member;

b) a peelable closure flap hingedly adhered to a peripheral portion of said first wall and sealing access to the pocket of the outer envelope, the closure flap terminating in a grip-facilitating tab whose free edge terminates a distance away from the bottom transverse edge of the outer envelope; and c) a combined surgical suture-needle device retainer member received within the pocket of the outer envelope;

wherein said combined surgical suture-needle device retainer member (c) includes means for exposing at least a portion of at least one of a needle and an attached suture upon peeling of said closure flap (b);

wherein said retainer member (c) possesses means for adhering to said closure flap (b) when said closure flap (b) is peeled away from said second wall;

wherein said retainer member (c) includes a main panel portion to retaining the suture and a fold-over panel portion attached to the main panel portion along a score line;

said means for adhering said retainer member (c) to said closure flap (b) comprising the bottom surface of said fold-over panel portion being adherently secured to the interior surface of said closure flap (b);

said main panel portion in non-adherent contact with said outer envelope (a);

whereby said package is opened in a single step by peeling of said closure flap, allowing access to the suture-needle combination contained therein without need to regrasp the package and whereby complete detachment of said closure flap (b) from said outer envelope (a) when said flap (b) is peeled, and accidental puncturing of said outer envelope (a) by the needle when said flap (b) is closed, are both prevented.

* * * * *